United States Patent
Filliers et al.

(10) Patent No.: US 7,456,287 B2
(45) Date of Patent: Nov. 25, 2008

(54) DIASTEREOSELECTIVE SYNTHESIS PROCESS FOR THE PREPARATION OF IMIDAZOLE COMPOUNDS

(75) Inventors: Walter Ferdinand Maria Filliers, Vremde (BE); Rudy Laurent Maria Broeckx, Turnhout (BE); Patrick René Angibaud, Fontaine-Bellenger (FR)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/568,426

(22) PCT Filed: Apr. 28, 2005

(86) PCT No.: PCT/EP2005/051934

§ 371 (c)(1),
(2), (4) Date: Oct. 27, 2006

(87) PCT Pub. No.: WO2005/105784

PCT Pub. Date: Nov. 10, 2005

(65) Prior Publication Data

US 2007/0238880 A1    Oct. 11, 2007

(30) Foreign Application Priority Data

May 3, 2004    (EP)    .................... 04076319

(51) Int. Cl.
*C07D 215/227*    (2006.01)

(52) U.S. Cl. ..................................................... 546/157
(58) Field of Classification Search ................ 546/290, 546/273.1, 272.7, 303, 157, 300; 548/364.7, 548/312.1

See application file for complete search history.

(56) References Cited

FOREIGN PATENT DOCUMENTS

| WO | WO 97/21701 A | 6/1997 |
|---|---|---|
| WO | WO 01/53289 A | 7/2001 |
| WO | WO 02/072574 A | 9/2002 |

OTHER PUBLICATIONS

Angibaud, P.R., et al. "Synthesis Routes Towards the Farnesyl Protein Transferase Inhibitor Zarnestra" European Journal of Organic Chemistry. vol. 3 (23004) pp. 479-486.
International Search Report PCT/EP2005/051934 mailed Dec. 7, 2005.

*Primary Examiner*—Bernard Dentz
*Assistant Examiner*—David E Gallis

(57) ABSTRACT

A diastereoselective synthesis process for the preparation of an enantiomer of 6-[amino(4-chlorophenyl)(1-methyl-1H-imidazol-5-yl)methyl]-4-(3-chlorophenyl)-1-methyl-2(1H)-quinolinone which comprises the conversion of (±)-6-[chloro(4-chlomphenyl)(1-methyl-1H-imidazol-5-yl)methyl]-4-(3-chlorophenyl)-1-methyl-2(1H)-quinolinone into a compound of formula (VIII) wherein aryl is phenyl substituted once or twice with $C_{1-6}$alkyloxy or naphtalenyl substituted once or twice with $C_{1-6}$alkyloxy.

10 Claims, No Drawings

DIASTEREOSELECTIVE SYNTHESIS PROCESS FOR THE PREPARATION OF IMIDAZOLE COMPOUNDS

CROSS REFERENCE TO RELATED APPLICCATIONS

This application is the national stage of Application No PCT/EP2005/051934, filed Apr. 28, 2005, which claims priority from EPO Patent Application No. 04076319.5 filed May 3, 2004, the entire disclosures of which are hereby incorporated in their entirety.

The present invention relates to the diastereoselective synthesis process of 5-substituted imidazole compounds which have farnesyl tranferase inhibitory activity and to compounds used in the synthesis process for said imidazole compounds.

Farnesyltransferase inhibitors block the main post-translational modification of the Ras protein, thus interfering with its localization to the inner surface of the plasma membrane and subsequent activation of the downstream effectors. Although initially developed as a strategy to target Ras in cancer, farnesyltransferase inhibitors have subsequently been acknowledged as acting by additional and more complex mechanisms that may extend beyond Ras involving GTP-binding proteins, kinases, centromere-binding proteins and probably other farnesylated proteins.

A particular farnesyltransferase inhibitor is described in WO 97/21701, namely (R)-(+)-6-[amino(4-chlorophenyl)(1-methyl-1H-imidazol-5-yl)methyl]-4-(3-chlorophenyl)-1-methyl-2(1H)-quinolinone. The absolute stereochemical configuration of the compound was not determined in the experiments described in the above-mentioned patent specification, but the compound was identified by the prefix "(B)" to indicate that it was the second compound isolated from column chromatography. The compound thus obtained has been found to have the (R)-(+)-configuration. This compound will be referred to below by its published code number R115777 and has the following formula (V).

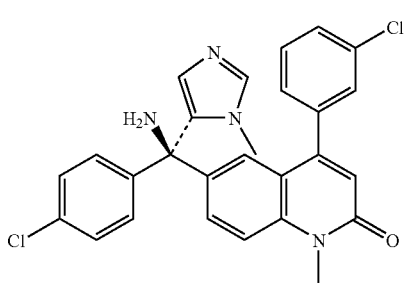

(V)

R115777 (Tipifarnib) is a potent, orally active inhibitor of farnesylprotein transferase. It is one of the most advanced of the farnesylprotein transferase inhibitors currently reported to be in clinical development, being one of the agents that have progressed to phase III studies.

R115777 has been found to have very potent activity against neoplastic diseases. Antineoplastic activity in solid tumors, such as breast cancer, as well as in haematological malignancies, such as leukemia, have been observed. Also combination studies have been carried out demonstrating that R115777 can be safely combined with several highly active anticancer drugs.

In WO 01/53289, the racemates (±)(4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one (racemate 1) and (±)4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one (racemate 2) are prepared.

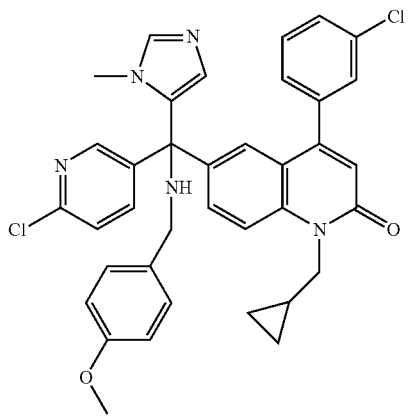

racemate 1

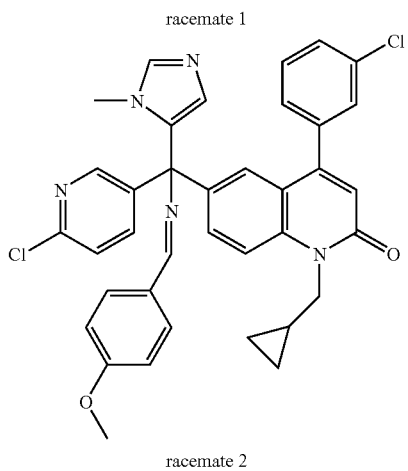

racemate 2

After chiral molecule separation using column chromatography, either the benzylamino or the benzilidine moiety of the resulting (+) and /for (−) enantiomers are converted to an amino group under acidic conditions.

The synthesis of R115777 as originally described in WO97/21701, is presented in scheme 1.

Herein, in step 1, the intermediate 1-methyl imidazole in tetrahydrofuran, is mixed with a solution of n-butyllithium in a hexane solvent to which is added chlorotriethylsilane (triethylsilyl chloride), followed by a further addition of n-butyllithium in hexane, the resulting mixture being cooled to −78° C. before the addition of a solution of a compound of formula (I), i.e. 6-(4-chlorobenzoyl)-4-(3-chlorophenyl)-1-methyl-2(1H)-quinolinone in tetrahydrofuran. The reaction mixture is subsequently brought to room temperature, and then hydrolysed, extracted with ethyl acetate and the organic layer worked up to obtain a compound of formula (II), i.e. (±)-6-[hydroxy (4-chlorophenyl)(1-methyl-1H-imidazol-5-yl)methyl]-4-(3-chlorophenyl)-1-methyl-2(1H)-quinolinone.

In step 2, the hydroxy compound of formula (II) is chlorinated with thionylchloride to form a compound of formula (III), i.e. (±)-6-[chloro(4-chlorophenyl)(1-methyl-1H-imidazol-5-yl)methyl]-4-(3-chlorophenyl)-1-methyl-2(1H)-quinolinone.

In step 3, the chloro compound of formula (III) is treated, with NH₄OH in tetrahydrofuran to form the amino compound of formula (IV), i.e. (±)-6-[amino(4-chlorophenyl)(1-methyl-1H-imidazol-5-yl)methyl]-4-(3-chlorophenyl)-1-methyl-2(1H)-quinolinone.

In step 4, the amino compound of formula (IV) is separated (into its enantiomers) and purified by chiral column chromatography over Chiracel OD (25 cm; eluent: 100% ethanol; flow: 0.5 ml/min; wavelength: 220 nm). The pure (B)-fractions are collected and recrystallised from 2-propanol resulting in R115777, the compound of formula (V).

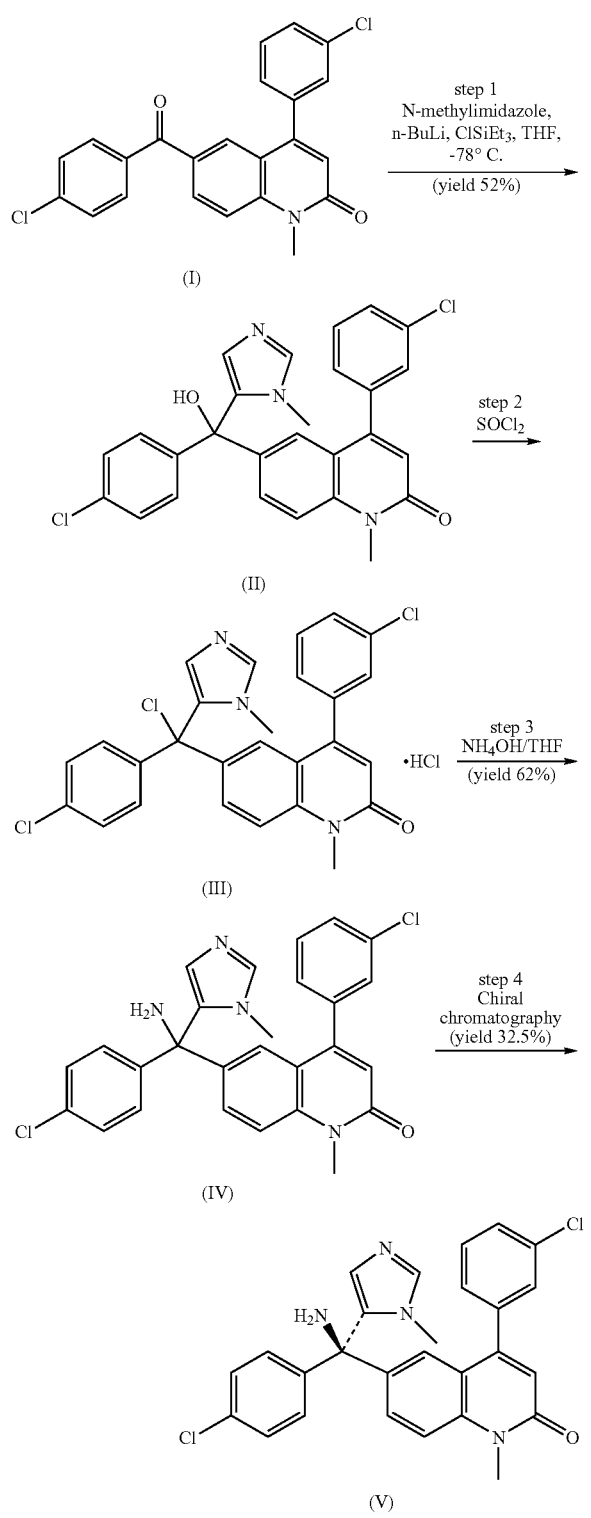

However, the procedure described in WO97/21701 has a number of disadvantages. For example, during the first step, the procedure results in the undesired formation of a corresponding compound of formula (IX), i.e. 6-[hydroxy(4-chlorophenyl)(1-methyl-1H-imidazol-2-yl)methyl]-4-(3-chlorophenyl)-1-methyl-2(1H)-quinolinone), in which the imidazole ring is attached to the remainder of the molecule at the 2-position of the ring, instead of the desired 5-position. At the end of the procedure, this results in the formation of a compound of formula (X), i.e. 6-[amino(4-chlorophenyl)(1-methyl-1H-imidazol-2-yl)methyl]-4-(3-chlorophenyl)-1-methyl-2(1H)-quinolinone.

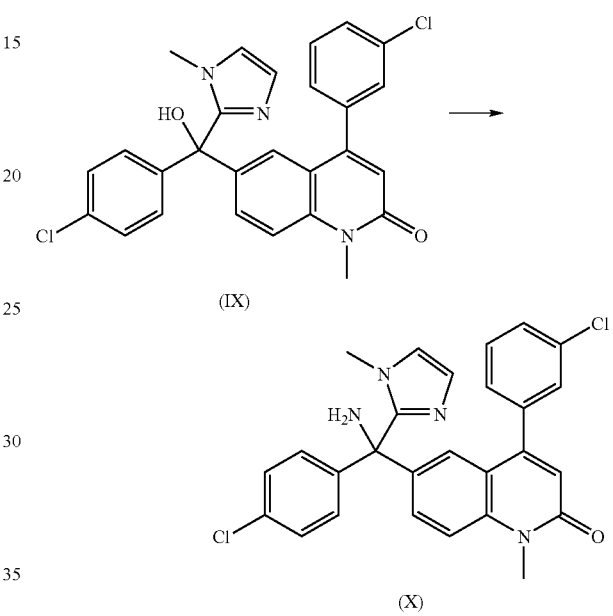

The use of n-butyllithium during the conversion of a compound of formula (I) in a compound of formula (II) is also undesirable in a commercial process in view of its pyrophoric nature and the formation of butane, a flammable gas, as the by-product. Also the carrying out of this process step, at a temperature as low as −78° C., is inconvenient and costly on a commercial scale.

Finally, the purification of compound (V) using chiral chromatography is expensive and disadvantageous in view of the large amounts of solvent needed and the specialised equipment required to perform a large scale chiral chromatography.

Another process for the synthesis of R115777 as described in WO 02/072574, is presented in scheme 2.

Herein, in step 1, 1-methyl imidazole in tetrahydrofuran is mixed with a solution of n-hexyllithium in a hexane solvent to which is added tri-iso-butylsilyl chloride, followed by a further addition of n-hexyllithium in hexane. The compound of formula (I) in tetrahydrofuran is then added to the reaction mixture, keeping the temperature between −5° C. and 0° C. The resulting product of formula (II) is isolated by salt formation.

In step 2, the chlorination reaction is effected by treatment of the compound of formula (II) with thionyl chloride in 1,3-dimethyl-2-imidazolidinone In step 3, the chloro compound of formula (III) is treated with a solution of ammonia in methanol. After the addition of water, the compound of formula (IV), precipitates and can be isolated.

In step 4, the compound of formula (IV) can be reacted with L-(−)-dibenzoyl tartaric acid (DBTA) to form the diastereomeric tartrate salt with formula (VI) i.e. R-(−)-6-[amino(4-chlorophenyl)(1-methyl-1H-imidazol-5-yl)methyl]-4-(3-chlorophenyl)-1-methyl-2(1H)-quinolinone [R—(R*,R*)]-2,3-bis(benzoyloxy)butanedioate (2:3).

Finally, in step 5, the compound of formula (VI) is treated with aqueous ammonium hydroxide, to form the crude compound of formula (V) which is then purified by recrystallisation from ethanol to the pure compound (V).

mula (IV) could preserve chirality. Several experimental conditions have been tested starting with an enantiomer of a compound of formula (II), but racemisation always occurred.

Another possibility was to enter chirality in the third step of the procedure. In a second study it was tried out if diastereoselective amination of a compound of formula (III) with a chiral amine, such as (R)-(+)-phenylethylamine was possible. It turned out that chirality could be introduced and the formation of a product such as 6-[(1-phenylethylamino)(4-chlorophenyl)(1-methyl-1H-imidazol-5-yl)]methyl-4-(3-chloro-

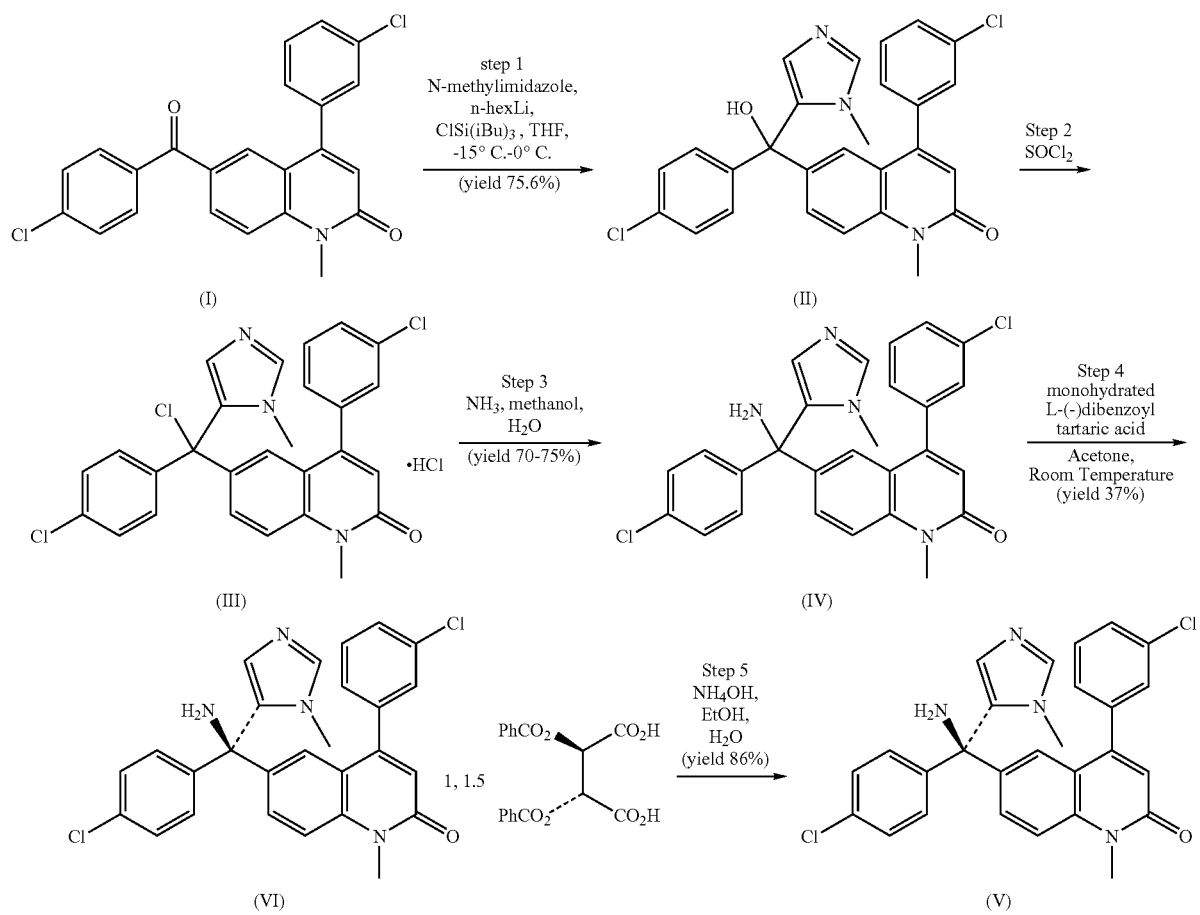

However, in view of the fact that water is present during the third and the fifth step of this procedure, there is significant formation of the hydroxy compound of formula (II).

This is important because the compounds of formula (II) and (V) are difficult to separate. In order to keep the quality of the final product (V) as high as possible, it is critical to limit the formation of compound (II).

The major drawback of the previous methods however is the generation of large amounts of the other enantiomer that subsequently must be recycled.

Attempts were made to develop processes that solve this problem. One of the possibilities was to enter chirality in the first step of the procedure. A first study was carried out in order to determine if the conversion of an enantiomer of the hydroxy compound of formula (II) into a compound of forrophenyl)-1-methyl-1H-quinolin-2-one (compound 14) (diastereomeric excess 40%) was possible.

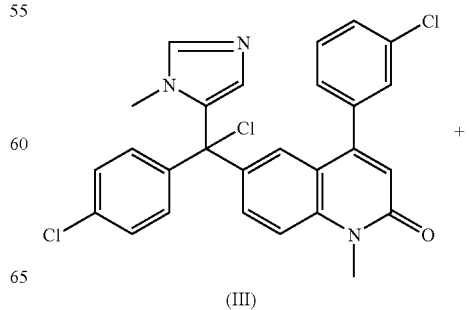

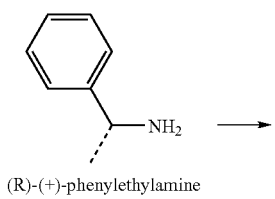

(R)-(+)-phenylethylamine

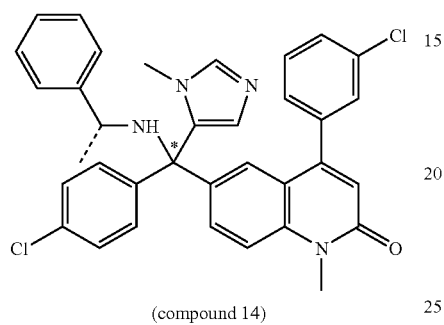

(compound 14)

However, subsequently it was find out that compound 14 could not be converted in an enantiomer of formula (IV). For example, treatment of compound 14 with trifluoro acetic acid in dichloromethane at a temperature between 0° C. and room temperature only gave the hydroxy compound of formula (II), while at a temperature of –10° C., compound 14 did not react. Other cleaving methods have been tried, such as, hydrogenation in the presence of (10%) paladium on carbon as catalyst or cleavage with α-chloroethyl chloroformate, but compound 14 respectively did not react or led to the formation of compound 17 i.e. (±)-6-[methoxy(4-chlorophenyl)(1-methyl-1H-imidazol-5-yl)methyl]-4-(3-chlorophenyl)-1-methyl-2(1H)-quinolinone.

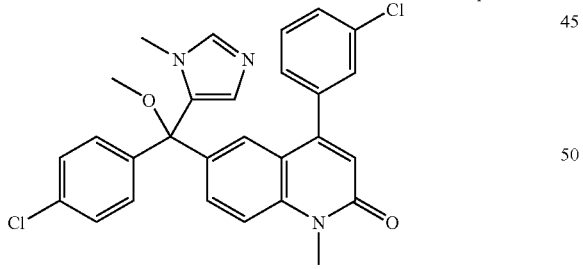

Compound 17

Finally, it was tried to perform the diastereoselective amination of a compound of formula (III) with the chiral amine described in the present invention.

Unexpectedly, diastereoselective synthesis introducing chirality in the third step of the process and subsequent conversion of the diastereomers in the enantiomers could be achieved and in addition no racemisation appeared during the fourth step.

Thus the present invention solves the above described problems. It provides a new process for the preparation of the compound of formula (IV) without the need to recycle one of the enantiomers while minimising the formation of undesired isomers and impurities and under conditions which offer economic advantages for operation on a commercial scale.

The present invention provides a process for the preparation of an enantiomer of formula (IV) which comprises a) converting the arylC$_{1-6}$alkylamino group of a compound of formula (VIII) wherein aryl is phenyl substituted once or twice with C$_{1-6}$alkyloxy or naphtalenyl substituted once or twice with C$_{1-6}$alkyloxy, to the amino group of an enantiomer of formula (IV), under acidic conditions, for example by addition of trifluoro acetic acid, in a suitable solvent, for example chlorinated hydrocarbons or tetrahydrofuran, at a suitable temperature, for example room temperature,

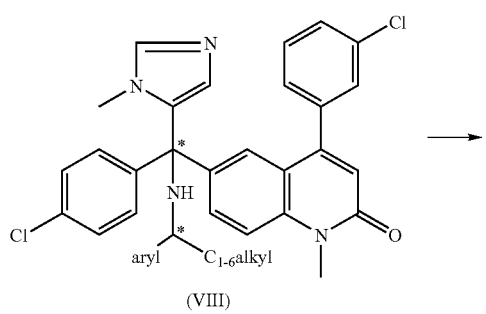

(VIII)

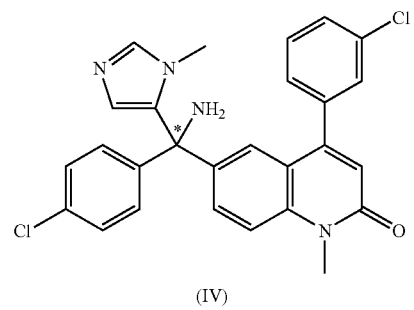

(IV)

b) the diastereoselective amination of a compound of formula (III) with a chiral amine of formula (VII) with the formation of a compound of formula (VIII), wherein aryl is phenyl substituted once or twice with C$_{1-6}$alkyloxy or naphtalenyl substituted once or twice with C$_{1-6}$alkyloxy.

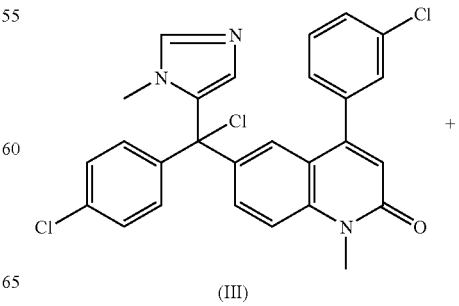

(III)

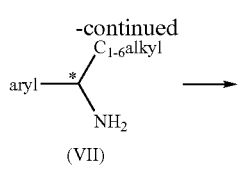

(VII)

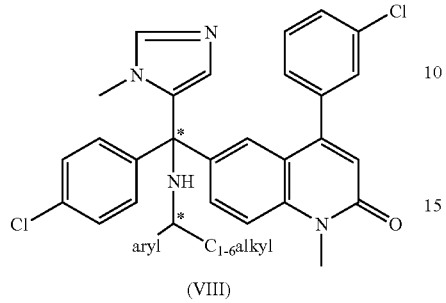

(VIII)

As used in the foregoing definitions and hereinafter $C_{1-6}$alkyl defines straight and branched chain saturated hydrocarbon radicals having from 1 to 6 carbon atoms such as, e.g. methyl, ethyl, propyl, butyl, 1-methylethyl, 2-methylpropyl, pentyl, 2-methyl-butyl, hexyl, 2-methylpentyl and the like.

In the above described process, the diastereomeric excess of a compound of formula (VIII) is 40% or higher, preferably higher than 60%, more preferably higher than 80%, most preferably higher than 94%. The two diastereomers can be further purified (from the other diastereomer) by standard techniques like crystallisation or chromatography.

After conversion of a compound of formula (VIII) into an enantiomer of formula (IV), racemisation or formation of a compound of formula (II) does not appear. The two enantiomers of a compound of formula (IV) can be further purified (from the other enantiomer) by standard techniques, such as crystallisation.

In step b) compounds of formula (III) are generally used in the reaction as a salt form, such as salts formed with HCl and hence, the number of equivalents of the chiral amine of formula (VII) used during the diastereoselective synthesis process of a compound of formula (IV) is generally two, preferably three or more.

In step b) 1-methyl-2-pyrrolidinone, N,N-dimethylformamide, acetonitrile, diglyme, 1,2-dimethoxyethane, chloroform and toluene can be used as solvents. Preferred solvents are dioxane and dichloromethane. The most preferred solvent is tetrahydrofuran.

The reaction time for the amination step is between 1 and 24 h, preferably between 1 and 12 h, more preferably between 1 and 5 h, most preferably between 1 h and 2 h 30 minutes.

It is common general knowledge that diastereomeric excess is higher when a diastereoselective process is performed at low temperatures. Unexpectedly, in the present invention, the influence of temperature is limited. The amination can be performed between −78° C. and 40° C., preferably between −40° C. and 40° C., more preferably between −10° C. and room temperature, most preferably between 0° C. and room temperature. The carrying out of this process step, at a temperature between 0° C. and room temperature is expedient on a commercial scale.

Preferably the chiral amine is added to a solution of a compound of formula (IV) and not vice versa.

In a preferred embodiment of the above described process the chiral amine is methoxyphenyl$C_{1-6}$alkylamine. In another preferred embodiment of the above described process the chiral amines are in the (S)-(−)-configuration. The most preferred chiral amine of formula (VII) in the above described process is (S)-(−)-1-(4-methoxyphenyl)ethylamine (intermediate 1).

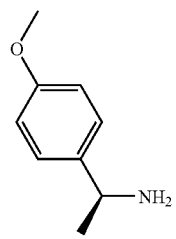

(intermediate 1)

In another preferred embodiment of the above described process the enantiomer of formula (IV) is the compound of the formula (V).

Another feature of the present invention is a compound of formula (VIII)

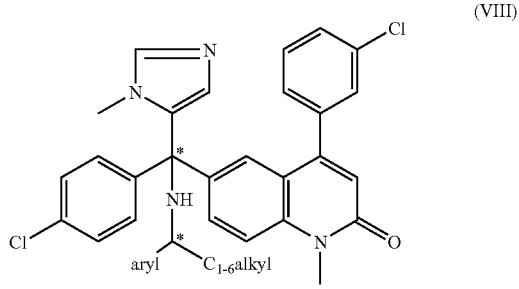

(VIII)

and the stereochemically isomeric forms thereof wherein aryl is phenyl substituted once or twice with $C_{1-6}$alkyloxy, or naphtalenyl substituted once or twice with $C_{1-6}$alkyloxy.

In a preferred embodiment, aryl in the compound of formula (VIII) is 4-methoxyphenyl. Preferred compounds of formula (VIII) are in the (R)-configuration. More preferred compounds of formula (VII) are compound 11, i.e. 6-[(4-methoxyphenyl)ethylamino)(4-chlorophenyl)(1-methyl-1H-imidazol-5-yl)]methyl-4-(3-chlorophenyl)-1-methyl-1H-quinolin-2-one and its diastereomers compounds 12 and compounds 13.

(compound 11)

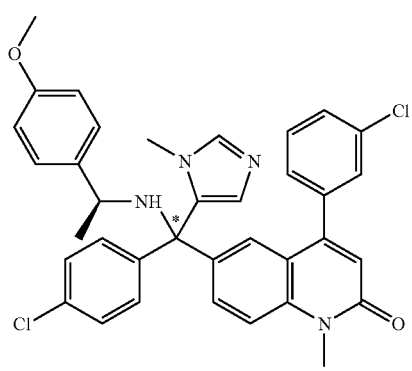

(compound 12)

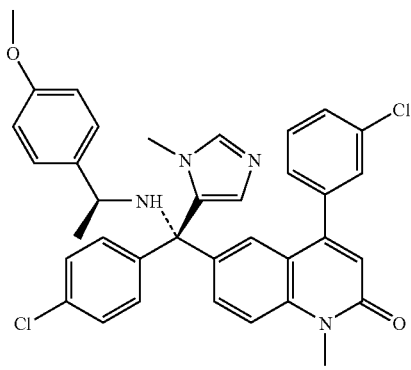

(compound 13)

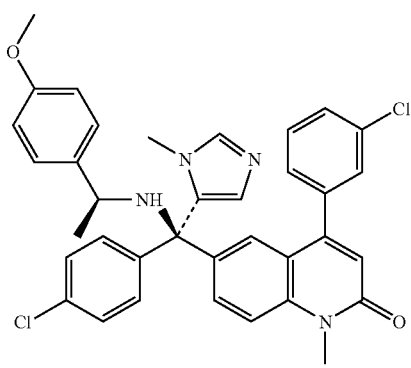

The most preferred compound of formula (VIII) is compound 13 (diastereomer (B) of compound 11).

(compound 13)

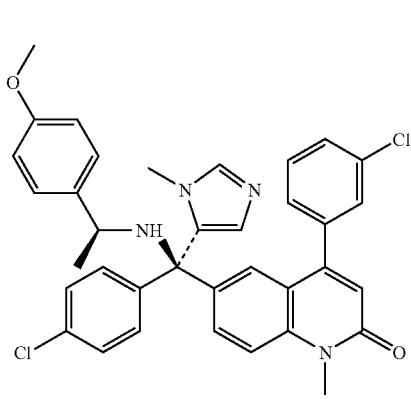

The pharmaceutically acceptable acid addition salts as mentioned hereinabove are meant to comprise the therapeutically active non-toxic acid and non-toxic base addition salt forms which the compounds of formula (VIII) are able to form. The compounds of (formula (VIII) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobroric acid; sulfuric; nitric; phosphoric and the like acids; or organic acids such as, for example, acetic, propanoic, hydroxyacetic, lactic, pyruvic, oxalic, malonic, succinic (ie. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The terms acid addition salt also comprise the hydrates and the solvent addition forms which the compounds of formula (VIII) are able to form. Examples of such forms are e.g. hydrates, alcoholates and the like.

The term stereochemically isomeric forms of compounds of formula (VIII), as used hereinbefore, defines all possible compounds made up of the same atoms bonded by the same sequence of bonds but having different three-dimensional structures which are not interchangeable, which the compounds of formula (VIII) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomneric forms of the compounds of formula (VIII) both in pure form or in admixture with each other are intended to be embraced within the scope of the present invention.

The term chiral amine of formula (VII) means an enantiomer of a compound of formula (VII), wherein the enantiomeric excess is 40% or higher, preferably higher than 60%, more preferably higher than 80%, most preferably higher than 94%.

The following examples illustrate the present invention.

Hereinafter "DCM" means dichloromethane, "EtOAc" means ethyl acetate, "MeOH" means methanol, "THF" means tetrahydrofuran and "$NH_4OAc$" means ammonium acetate.

A. Preparation of Intermediates

EXAMPLE A.1 a) Preparation of 6-[((R)-1-phenylethylamino)(4-chlorophenyl)(1-methyl-1H-imidazol-5-yl)]methyl-4-(3-chlorophenyl)-1-methyl-1H-quinolin-2-one (compound 14)

(compound 14)

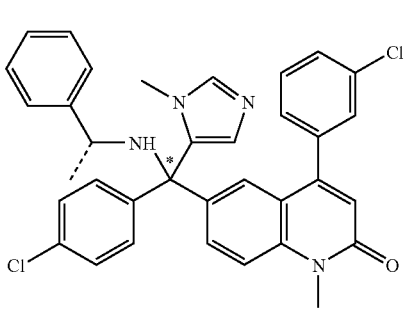

(R)-(+)-phenylethylamine (0.0097 mol) was added at 0° C. to a solution of compound (III)(0.0019 mol) in THF (10 ml). The mixture was stirred at room temperature for 1 hour Water was added. The mixture was extracted with EtOAc. The organic layer was separated, dried ($MgSO_4$), filtered, and the solvent was evaporated. The obtained fraction was purified by column chromatography on silica gel (40 μm)(eluent: $CH_2Cl_2$/MeOH/$NH_4OH$ 97/3/0.5), yielding 0.6 g (52%) of compound 14, melting point 122° C., diastereomeric excess 40%.

b) Preparation of Compound 15 and Compound 16

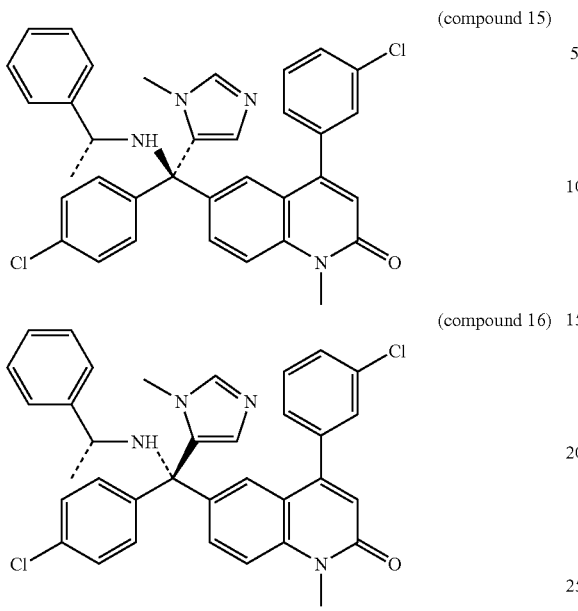

(compound 15)

(compound 16)

Compound 14 was purified by column chromatography over silica gel (10 µm) (eluent: MeOH/NH$_4$OAc 78/22). The fractions were collected and the solvent was evaporated, yielding 0.026 g of diastereoisomer (A), melting point 138° C. and 0.114 g diastereoisomer (B), melting point 134° C. Both diastereomers were taken up in DCM and the mixtures were evaporated giving 0.016 g diastereoisomer (A) and 0.082 g diastereoisomer (B).

EXAMPLE A.2 a) Preparation of 6-[((S)-1-(4-methoxyphenyl)ethylamino)(4-chlorophenyl)(1-methyl-1H-imidazol-5-yl)]methyl-4-(3-chlorophenyl)-1-methyl-1H-quinolin-2-one (compound 11)

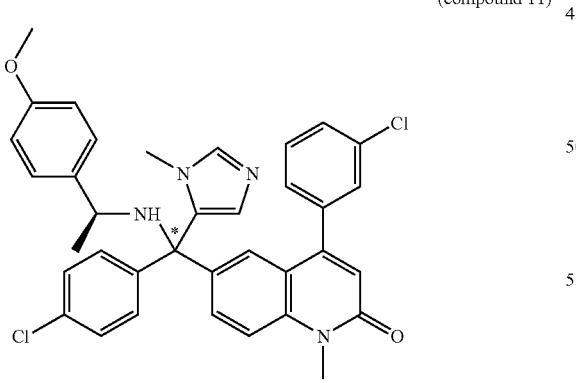

(compound 11)

(S)-(−)-1-(4-methoxyphenyl)ethylamine (intermediate 1) (0.0153 mol) was added quickly at room temperature to a solution of compound (III) (0.003 mol) in TUF (10 ml). The mixture was stirred at room temperature for 1 hour and 30 minutes. Water was added. The mixture was extracted with DCM. The organic layer was separated, dried (MgSO$_4$), filtered, and the solvent was evaporated. The obtained fraction was purified by column chromatography on silica gel (15-40 µm)(eluent: CH$_2$Cl$_2$/MeOH/NH$_4$OH 97/3/0.2), yielding 0.8 g (41%) of compound 11, melting point 130° C., diastereomeric excess 44%.

b) Preparation of Compound 12 and Compound 13

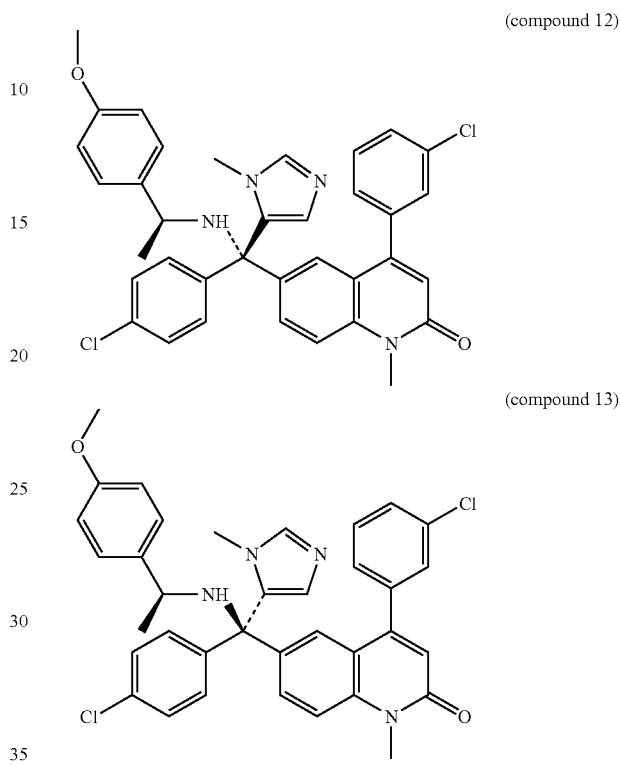

(compound 12)

(compound 13)

Compound 11 was purified by column chromatography over silica gel (10 µm)(eluent: MeOH/NH$_4$OAc 78/22). The fractions were collected and the solvent was evaporated, yielding: 0.036 g of diastereoisomer (A)(compound 12), melting point 132° C. and 0.178 g diastereoisomer (B)(compound 13), melting point 128° C.

B. Preparation of Final Compounds

EXAMPLE B.1 a) Attempt to Prepare Compound (IV) and the Resulting Preparation of Compound (II)

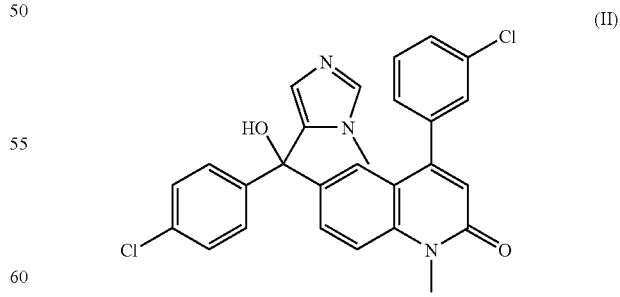

(II)

Trifluoro acetic acid (0.55 ml) was added at 0° C. to a solution of compound 14 (0.00015 mol) in DCM (0.55 ml). The mixture was stirred at room temperature for 30 minutes. DCM was added. The mixture was added to potassium carbonate (10%) on ice. The organic layer was separated, washed with a solution of saturated sodium chloride, dried (MgSO$_4$), filtered, and evaporated giving 0.072 g (100%) of compound (II), melting point 234° C., enantiomeric excess 2%.

b) Attempt to Prepare Compound (IV) and the Resulting Preparation of Compound 14

(compound 14)

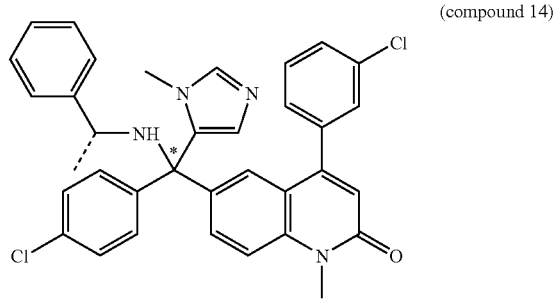

Compound 14 (0.0004 mol) and palladium on carbon (10%) (0.00047 mol) were added to ethanol (80 ml). The mixture was stirred at room temperature under hydrogenic atmosphere (3 bars) for 24 hours. The reaction mixture was filtered through celite, washed with DCM and evaporated, yielding 0.25 g (100%) of compound 14.

c) Attempt to Prepare Compound (IV) and the Resulting Preparation of (±)-6-[methoxy(4-chlorophenyl)(1-methyl-1H-imidazol-5-yl)methyl]-4-(3-chlorophenyl)-1-methyl-2(1H)-quinolinone (compound 17)

(compound 17)

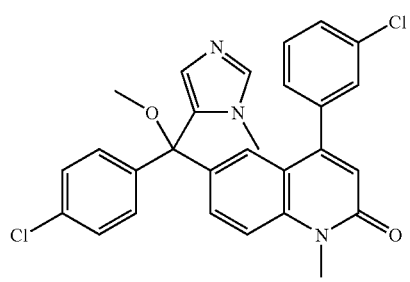

Compound 14 (0.00034 mol) and α-chloroethyl chloroformate (0.00054 mol) were refluxed with DCM (1.5 ml) for 2 hours and evaporated. The fraction was refluxed with MeOH (2 ml) for 1 hour and evaporated, yielding 0.274 g of compound 17.

EXAMPLE B.2 a) Preparation of Compound (V)

compound (V)

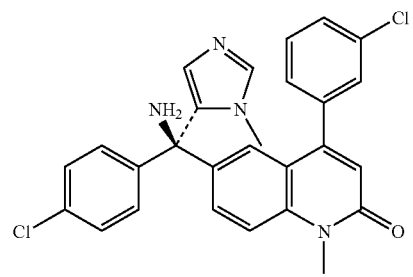

Trifluoro acetic acid (1.6 ml) was added at 0° C. to a solution of compound 11 (0.00015 mol) in DCM (1.6 ml).

The mixture was stirred at room temperature for 35 minutes. DCM was added. The mixture was added to potassium carbonate (10%) on ice. The organic layer was separated, washed with a solution of saturated sodium chloride, dried (MgSO$_4$), filtered, and evaporated giving 0.21 g (100%) of compound (V), melting point 214° C., enantiomeric excess 40%, content of compound (II)<0.5%.

The invention claimed is:

1. A process for the preparation of an enantiomer of formula (IV) which comprises a) the diastereoselective amination of a compound of formula (III) with a chiral amine of formula (VII) thereby forming a compound of formula (VIII), wherein aryl is phenyl or naphthalenyl substituted once or twice with $C_{1-6}$alkyloxy;

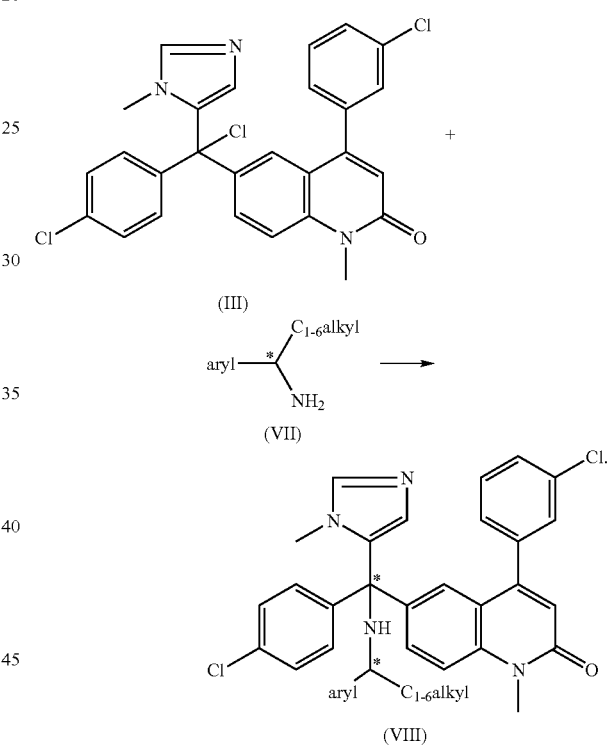

b) and converting the aryl$C_{1-6}$alkylamino group of the compound of formula (VIII) under acidic conditions, to the amino group of an enantiomer of formula (IV)

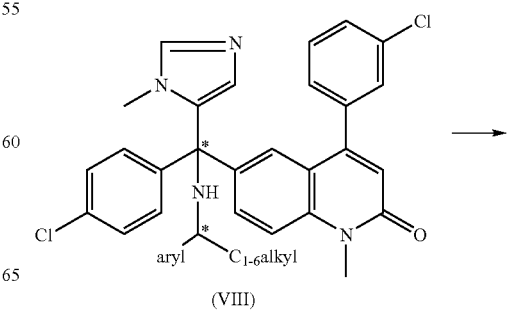

-continued

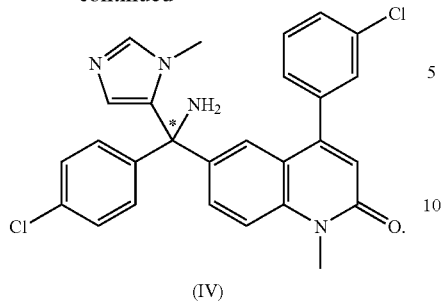

(IV)

2. A process as claimed in claim 1, wherein the compound of formula (VIII) is employed in a diastereomeric excess of 40% or higher in step a.

3. A process as claimed in claim 1 wherein the chiral amine of formula (VII) is in the (S)-(−)-configuration.

4. A process as claimed in claim 1 wherein the chiral amine of formula (VII) is (S)-(−)-1-(4-methoxypheyl)ethylamine (intermediate 1), (intermediate 1)

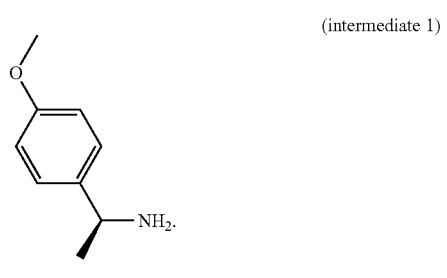

5. A process as claimed in claim 1 wherein
a) the solvent used in the amination step b) is tetrahydrofuran,
1,) the reaction time in the amination step b) is between 1 and 2 h 30 minutes,
c) the amination step b)is performed at a temperature between 0° C. and room temperature, and
d) the chiral amine of formula (VII) is added to the solution of a compound of formula (III).

6. A process as claimed in claim 1 wherein the compound of formula (VIII) is in the (R)-configuratian.

7. A process as claimed in claim 1 wherein the compound of formula (VIII) is compound 13, (compound 13)

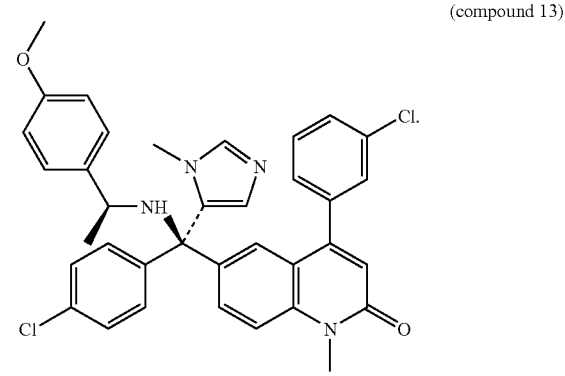

8. A process as claimed in claim 1 wherein the enantiomer of formula (IV) is the compound of the formula (V), compound (V)

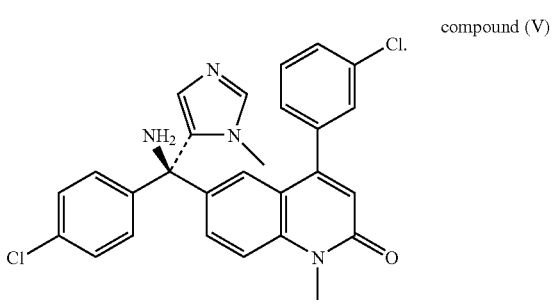

9. A compound of formula (VIII)

(VIII)

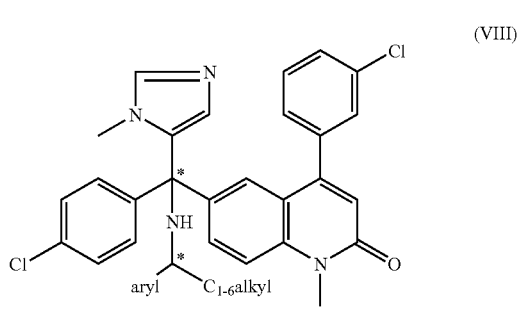

and the stereochemically isomeric forms thereof wherein aryl is phenyl or naphthalenyl substituted once or twice with $C_{1-6}$alkyloxy.

10. A compound of formula (VIII) as claimed in claim 9 wherein the compound is selected from the group consisting of: compound 11 and its diastereomers compound 12 and compound 13, (compound 11)

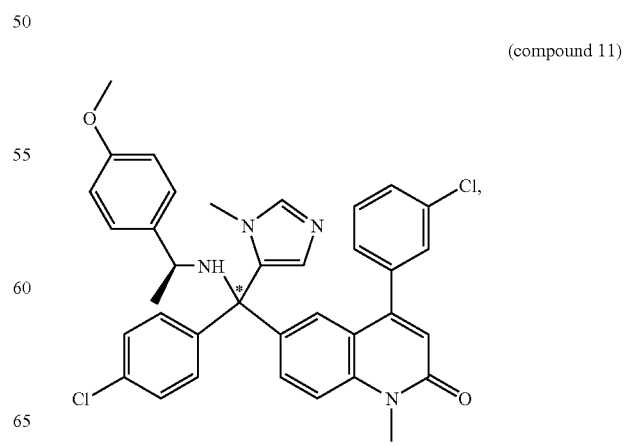

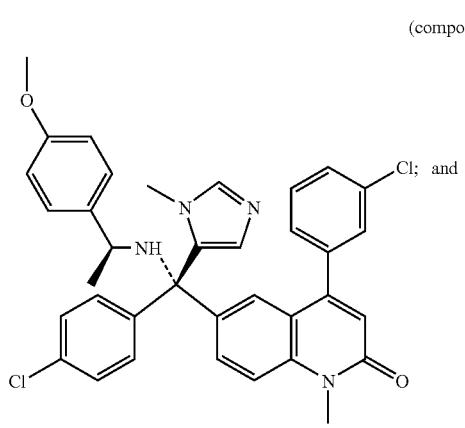
(compound 12)
Cl; and
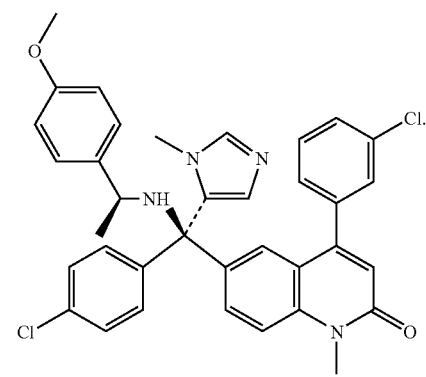
(compound 13)
* * * * *

UNITED STATES PATENT AND TRADEMARK OFFICE
CERTIFICATE OF CORRECTION

PATENT NO.         : 7,456,287 B2                                            Page 1 of 1
APPLICATION NO.    : 11/568426
DATED              : November 25, 2008
INVENTOR(S)        : Walter Ferdinand Maria Fillier et al.

It is certified that error appears in the above-identified patent and that said Letters Patent is hereby corrected as shown below:

Column 17, Claim 5 b) is incorrectly listed as "1,)". Please correct to read "b)".

Column 18, Claim 10: Compound 11 has the uppermost Cl abbreviation listed with a comma. Please remove the comma so only "Cl" is listed.

Signed and Sealed this

Twenty-second Day of December, 2009

David J. Kappos
*Director of the United States Patent and Trademark Office*